United States Patent [19]

Seyed-Yagoobi

[11] Patent Number: 4,790,668

[45] Date of Patent: Dec. 13, 1988

[54] VISCOMETRIC THERMOMETER

[75] Inventor: Jamal Seyed-Yagoobi, Bryan, Tex.

[73] Assignee: Westvaco Corporation, New York, N.Y.

[21] Appl. No.: 145,136

[22] Filed: Jan. 19, 1988

[51] Int. Cl.$^4$ .................. G01N 11/00; G01N 25/00
[52] U.S. Cl. ............................................ 374/54; 73/55; 374/135
[58] Field of Search ............... 374/54, 57, 135; 73/59, 73/55

[56] References Cited

U.S. PATENT DOCUMENTS

| | | | |
|---|---|---|---|
| 503,337 | 8/1893 | Uehling . | |
| 2,356,607 | 8/1944 | O'Brien | 374/135 |
| 3,082,620 | 3/1963 | Brazier | 73/54 |
| 4,478,071 | 10/1984 | Lecacheux et al. | 73/55 |
| 4,578,990 | 4/1986 | Abbott et al. | 73/55 |
| 4,603,979 | 8/1986 | Matilainen et al. | 374/54 |

OTHER PUBLICATIONS

"The Viscometric Thermometer: A Non-Perturbing Instrument for Measuring Temperature in Tissues Under Electromagnetic Radiation" by M. M. Chen, C. A. Cain, K. L. Lam and J. Mullin, published in Journal of Bioengineering, vol. 1, 1977, pp. 547-554.
"Viscometric Temperature Measurement in Electric or Magnetic Fields" by J. Seyed-Yagoobi, J. C. Chato and J. M. Crowley, published in the Review of Scientific Instruments, vol. 55, No. 9, Sep. 1984, pp. 1471-1474.

Primary Examiner—Daniel M. Yasich
Attorney, Agent, or Firm—W. A. Marcontell; R. L. Schmalz

[57] ABSTRACT

A viscometric thermometer is fabricated with two sensing capillaries connected serially in a common fluid flow circuit. The first capillary is immersed in a reference bath of known constant temperature. Pressure differential across the first capillary is measured and the fluid medium flow rate through the common circuit is determined. The second sensor is positioned in the unknown temperature environment and pressure differential across the second capillary is measured. This second capillary pressure differential is combined with the determined flow rate value to further determine the unknown temperature value.

8 Claims, 4 Drawing Sheets

VISCOMETRIC THERMOMETER

BACKGROUND OF THE INVENTION

1. Field Of The Invention

This invention relates to the quantified measurement of temperature. More specifically, the invention relates to viscometric thermometers having no metallic components.

2. Prior Art

Conventional thermometric methods and instruments are not suitable for use in strong electric or magnetic fields such as microwave frequencies because of (a) perturbations in the field caused by conductive components of the sensor and/or instrumentation or (b) direct heating of the sensor by the electric or magnetic field. Although techniques have been developed to minimize field effect consequences on thermistor and thermocouple probes, it has proven impossible to completely eliminate such interactions.

Viscometric temperature measurement has origins before the beginning of the twentieth century. U.S. Pat. No. 503,337 issued Aug. 15, 1893 to E. A. Uehling and A. Steinbart describes a device designed to function with viscometric principles albeit the principles themselves are not explained. Conceptively, the technique is predicated on the known relationship between temperature and viscosity for a given fluid medium. Recently, this basic concept has been exploited in two ways. By one procedure, the fluid medium is pumped through a capillary sensing element at a constant flow rate. Temperature is derived as a function of measured pressure differential across the capillary. By the other procedure, the fluid medium is driven through the capillary sensing element by a constant pressure head and temperature is derived as a function of measured flow rate.

The Journal of Bioengineering, Vol. 1, 1977, pp 547–554 publication "The Viscometric Thermometer: A Non-Perturbing Instrument For Measuring Temperature In Tissues Under Electromagnetic Radiation" by M. M. Chen et al describes the theory and implementation of a constant flow rate instrument.

Review of Scientific Instruments, Vol. 55, No. 9, Sept. 1984, pp 1471–1474, in the article "Viscometric temperature measurement in electric or magnetic fields," by J. Seyed-Yagoobi et al describes a constant pressure system of viscometric thermometry.

Although both of the foregoing procedures are accurate and reliable for steady state temperature measurement, transient response is less than desirable.

It is therefore, an object of the present invention to provide a viscometric thermometer having an accurate response interval of 3 to 4 seconds.

Another object of the present invention is to teach a thermetric measuring procedure that utilizes only non-ionizing or conductive components in the sensory zone.

Another object of the present invention is the construction of a constant pressure mode viscometric thermometer having improved accuracy and responsiveness.

SUMMARY

These and other objects of the invention are accomplished by a viscometric thermometer method and apparatus having two sensing capillaries in series circuit with a constant pressure flow drive. The first sensing capillary is immersed in a fluid bath having a known and constant temperature. Pressure differential across the first capillary is measured. From this datum, the flow rate is determined which must, necessarily, be the same as that of the second capillary: which is subjected to the environment of interest. Pressure differential across the second sensing capillary is determined by direct measurement which is then combined with the flow rate conclusion from the first capillary for determination of the interest environment temperature.

BRIEF DESCRIPTION OF THE DRAWINGS

Relative to the drawings wherein like reference characters designate like or similar elements throughout the several figures of the drawings.

PREFERRED EMBODIMENT

Figure 1:
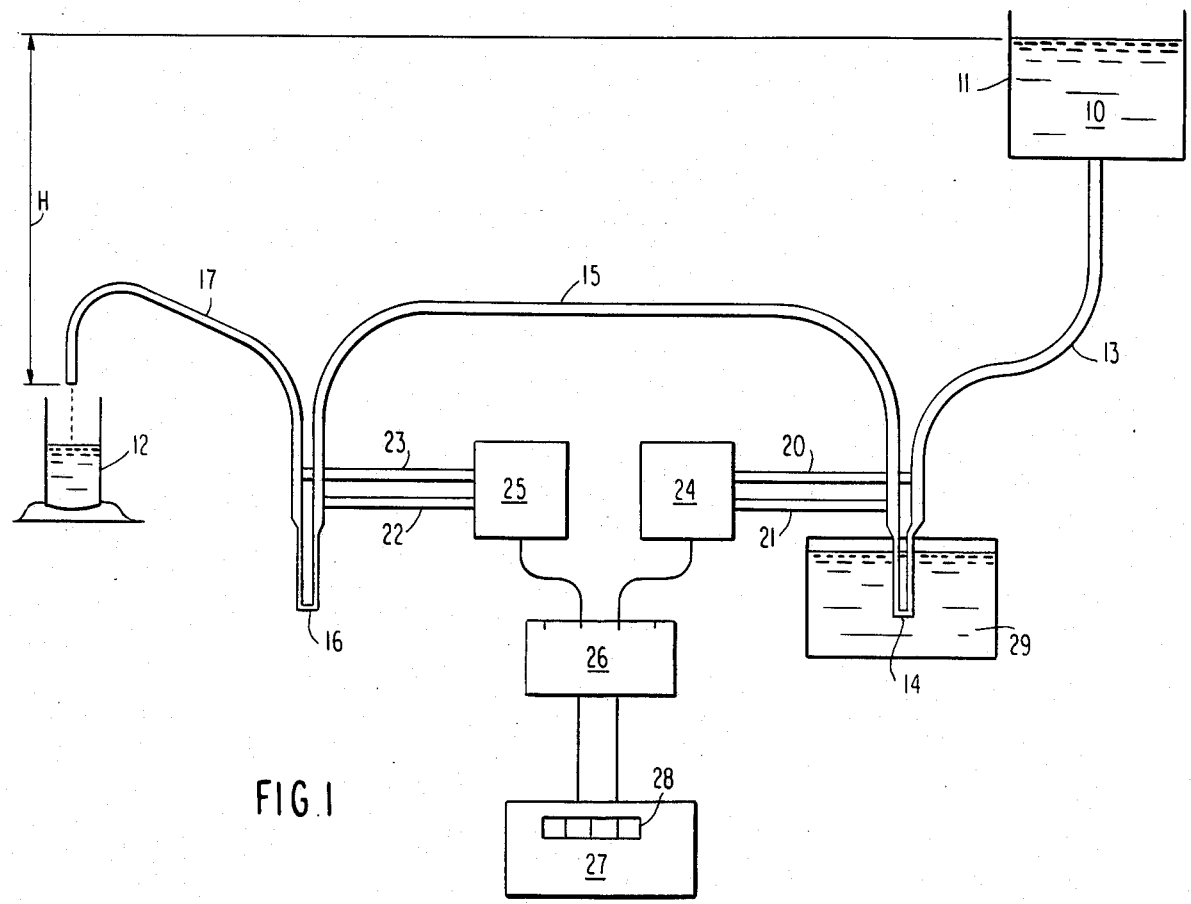
FIG. 1 is a flow schematic of the invention.

The present invention is represented in its most fundamental embodiment by the schematic of FIG. 1 wherein a fluid medium 10 such as a light petroleum oil or glycerine is carried in a continuously closed series circuit between a supply reservoir 11 and a receiver 12. As taught by Uehling et al, gaseous fluids such as air or nitrogen may also be used. A constant pressure differential is maintained between the supply and receiving reservoirs as represented by the differential head dimension, H.

Three plastic tubing conduit sections 13, 15 and 17 linked by two capillary sections 14 and 16 form a flow channel between the supply and receiving reservoirs. Junctioned with the flow channel, before and after each capillary section, are static pressure conduits 20, 21, 22, and 23. The static pressure conduit pair 20, 21 is connected to a pressure differential transducer 24 and the conduit pair 22, 23 connected to pressure differential transducer 25. Both transducers convert fluid pressure differential quantities between respective conduit pairs to corresponding electrical quantities which are conducted to an analog-to-digital (A/D) converter 26. The A/D converter transforms the electrical analog signals into corresponding digital signals which, in turn, are conducted to appropriate data input terminals of a computer 27. The temperature quantity measured by the apparatus at capillary section 16 is displayed digitally by light emitting diode (LED) array 28.

Figure 2:
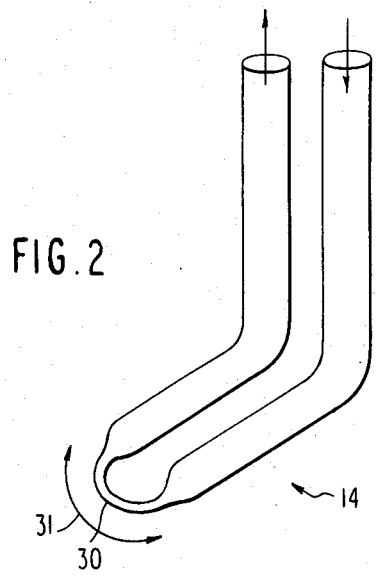
FIG. 2 is an enlarged, detail view of a representative sensing capillary used with the invention.

Constructionally, the capillary sections 14 and 16 may be identical. FIG. 2 shows a detailed representation of section 14. Glass is a suitable fabrication material. In a specific embodiment of the FIG. 2 capillary, a sensory tip 30 having a 4 mm arc length 31 was drawn to an inside capillary diameter of 0.1 to 0.17 mm. This restriction created a pressure loss between the junctions of conduits 20 and 21 at least fifteen times greater than the sum of all losses from the flexible tubing conduit sections 13, 15 and 17: thus serving one of the essential construction parameters of the invention that the pressure differentials across the capillary tips represent the dominant pressure losses in the system.

Another essential construction parameter for the invention is that the fluid medium 10 attains equilibrium temperature with the environment surrounding each capillary section while in transit along the capillary length. This constraint will influence the capillary size and material selection as it relates to heat transfer rate.

Figure 3:
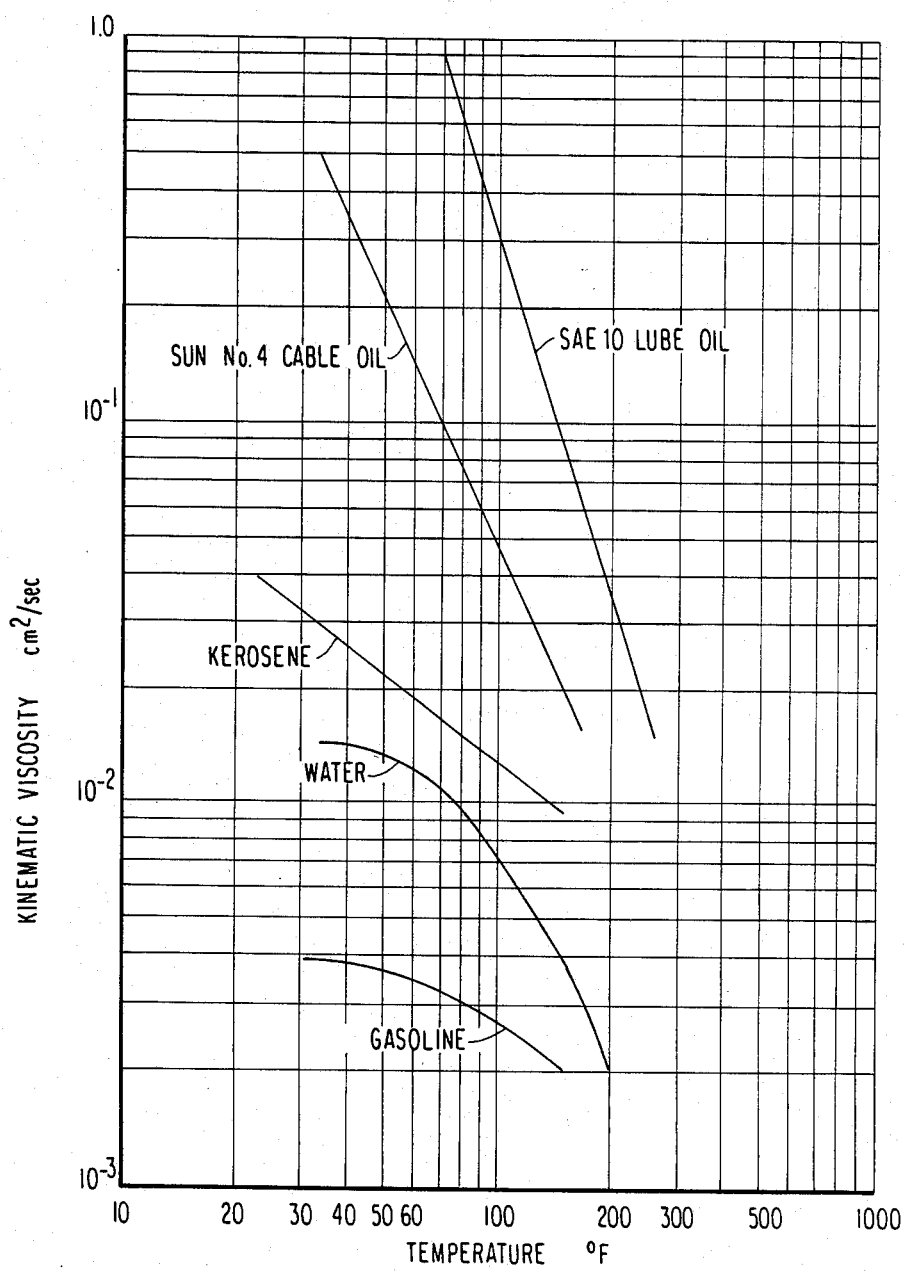
FIG. 3 is a graph showing the temperature and viscosity correlation of several common liquids suitable for use in the invention.

Fluid medium material selection is also influenced by the thermal equilibrium requirement. Whether gas or liquid, the correlation between temperature T, and dynamic viscosity $\mu$ for the temperature range suspected of the environment surrounding sensing capillary 16 must be known. This relationship is usually developed empirically from actual test data. The FIG. 3 graph is representative. For most liquids, the factor $T/\mu$ is an exponential function programmed into the computer 27 prior to instrument use. Responsiveness and accuracy will bias the fluid medium material selection toward that material having the greatest $\Delta T/\Delta \mu$ ratio for the temperature range an investigator seeks to measure.

For the reference capillary 14, the ambient environment is a temperature controlled bath 29. Hence, the fluid medium temperature/$T_1$ as it courses through the reference capillary 14, is a known and constant value. The unknown temperature/$T_2$ of the environment surrounding sensor capillary 16 is the measurement objective of the invention. However, as a consequence of both pressure differential transducers 24 and 25, the pressure losses across both capillary sections 14 and 16, $\Delta p_1$ and $\Delta p_2$, are also known values.

Correlating these known and unknown values is the fundamental fluid flow relation:

$$Q = C\nu^{-1}$$

where
Q = fluid flow rate
$\nu = f(T°) =$ kinematic viscosity
$C = (\pi/128)(D^4/L)(gH)$
and
D capillary flow diameter
L capillary flow length
g gravitational acceleration
H system driving pressure Accordingly, the instantaneous flow rate $Q_1$ through the system at the reference sensor 14 will be:

$$Q_1 = (\pi/128)(D_1^4/L_1)(\Delta p_1/\mu_1)$$

In this relation, $D_1$ and $L_1$ are constant capillary dimensions for flow diameter and length, respectively. $\Delta p_1$ is the pressure differential value measured by transducer 24. $\mu_1$ is the dynamic viscosity of the fluid medium 10 at the known temperature $T_1$ of the controlled temperature capillary bath 29. From the experimentally derived relationship between temperature and viscosity for the specific fluid medium 10 used, $\mu_1$, is therefore determinable. Hence, the system flow rate $Q_1$ is determinable.

Due to the serial circuitry of the instrument sysem, the flow rate $Q_1$ at the reference capillary 14 is identical to the simultaneous flow rate $Q_2$ at the sensor capillary 16.

$$Q_1 Q_2$$

From the foregoing assumptions and determinations:

$$Q_1 = Q_2 = (\pi/128)(D_2^4/L_2)(\Delta p_2/\mu_2)$$

ti and $$\mu_2 = (\pi/128)(D_2^4/L_2)(\Delta p_2/Q_2)$$

Once again, the physical dimensions of the sensor capillary 16, $D_2$ and $L_2$ are known. Pressure drop across the sensor capillary $\mu p_2$ is measured by transducer 25. The flow rate through the sensor capillary 16, $Q_2$, is known from the prior determination of $Q_1$. Accordingly, the fluid medium 10 dynamic viscosity $\mu_2$ is determinable. From the experimentally derived $T/\mu$ relationship. $T_2$ is determinable.

Figure 4:
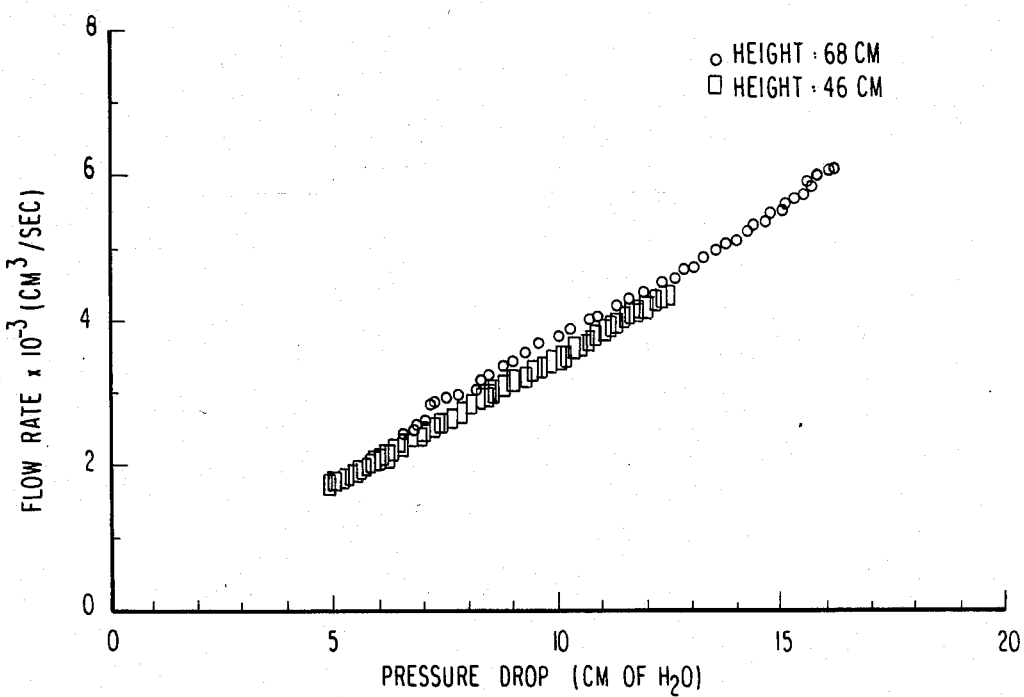
FIG. 4 graphs the correlation between fluid medium flow rate and pressure loss across a reference capillary at two total head values.
Figure 5:
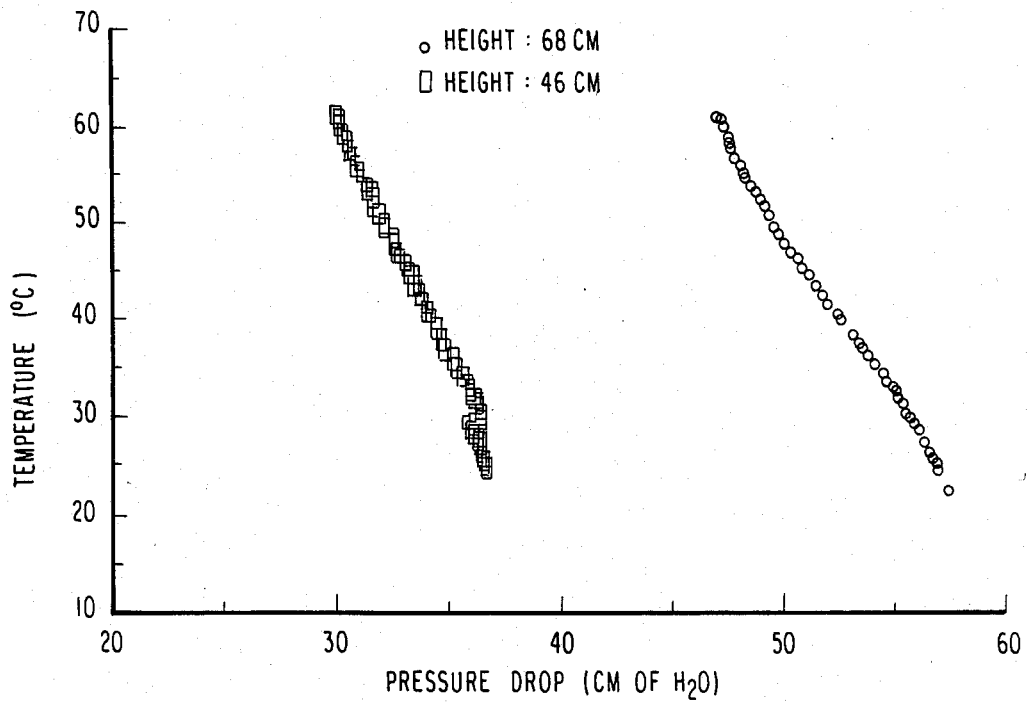
FIG. 5 graphs the correlation between fluid medium temperature and pressure loss across a sensor capillary at two total head values.
Figure 6:
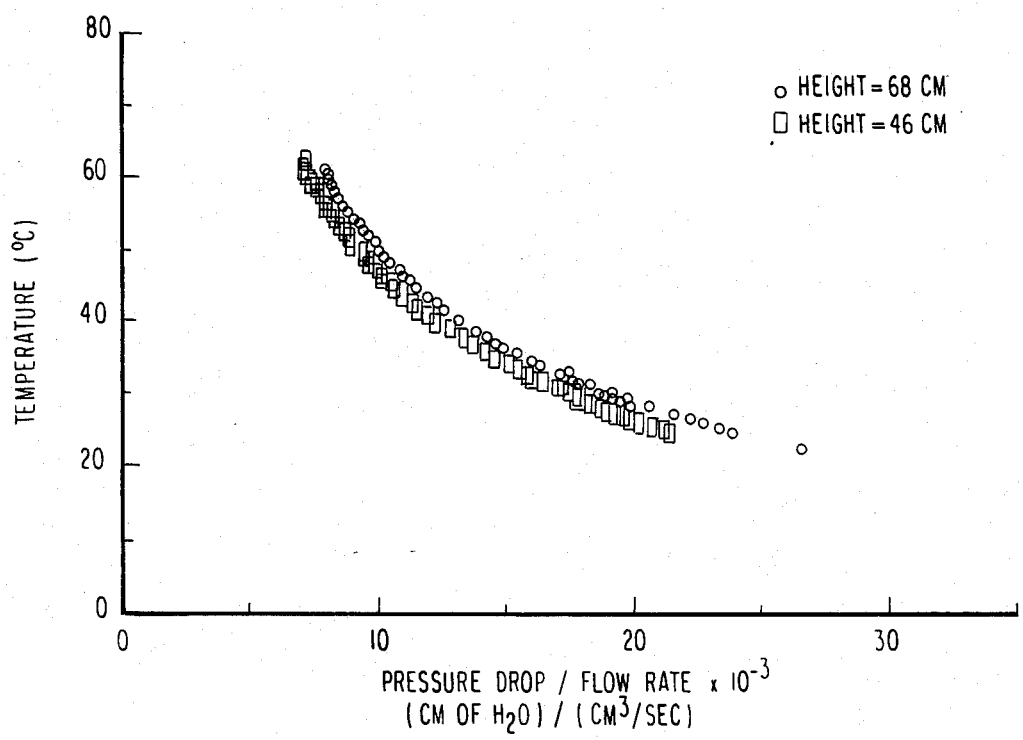
FIG. 6 graphs the correlation between fluid medium temperature and the ratio of pressure loss across a sensor capillary to system flow rate at two total head values.

The graphs of FIGS. 4, 5 and 6 are presented to illustrate the accuracy and stability of a specific embodiment of the invention using No. 4 Sun oil, a cable oil product of the Sun Oil Company.

FIG. 4 illustrates calibration data from the reference capillary 14 and shows the pressure drop across the capillary, $\Delta p_1$, as linearly proportional to the system flow rate, $Q_1$.

FIG. 5 shows the pressure loss $\Delta p_2$ across the sensor capillary 16 as a function of the measured sensor environment temperature, $T_2$. Since the pressure loss is also a function of flow rate $Q_2$, the relationship is parametrically dependent on the system drive pressure H. FIG. 6 shows the same data as FIG. 5 but with the drive pressure factor substantially normalized out of the relation by plotting the abscissa as the ratio of the pressure drop and flow rate, $\Delta p_2/Q_2$. Note that the two loci corresponding to respective drive pressures H substantially coincide.

The foregoing analytical development explains the theoretical basis of the invention and, in part, the program mechanics of the computer 27. In practice, however, use of the invention is considerably simplified.

For a given apparatus and fluid medium, there are only two measured variables, i.e. the two capillary pressure differentials $\Delta p_1$ and $\Delta p_2$. These two measured variables are correlated, in a specific apparatus using a specific fluid medium, to an unknown temperature, $T_2$, by implementation of a two-stage calibration program.

With a specific fluid at the known reference temperature, $T_1$, the first calibration program is based upon a parametric series of known flow rates, $Q_1$, induced through the apparatus and the corresponding reference capillary 14, $\Delta p$, values recorded. Using an interpolation program, the computer 27 can thereafter determine the value of an unknown flow rate $Q_1$, from the singular input value of $\Delta p_1$: assuming, of course, the same apparatus, fluid medium and reference temperature $T_1$.

The second calibration program correlates the first program determined flow rate Q to an unknown temperature $T_2$ surrounding the sensor capillary 16. Data for developing the second calibration program is also based upon a parametric series of known flow rates, Q. At each of several known flow rates, Q, a calibration relationship is recorded for the sensor capillary pressure differentials $\Delta p_2$ resulting from a known sensor capillary temperature range $T_2$. An interpolation program supports the primary, data based, program.

From these two calibration programs and direct computer entry of the $\Delta p_1$ and $\Delta p_2$ values, the objective temperature $T_2$ is read directly from the LED array 28. From the $\Delta p_1$ value and the first calibration program, the computer 28 determines the corresponding flow rate Q. Referencing the determined flow rate, Q, the computer selects the appropriate second calibration program. From the appropriate second program, a measured input value of sensor capillary pressure differential $\Delta p_2$ specifies the corresponding temperature, $T_2$.

Having fully describes my invention,

I claim:

1. An apparatus for measuring the temperature of a designated environment comprising:

A fluid flow conduit connected between a fluid flow drive of substantially constant pressure differential;

At least two heat sensing capillaries in series flow circuit with said conduit;

Pressure differential detecting means connected to said fluid flow conduit respective to each sensing capillary for measuring fluid flow pressure differential across respective sensing capillaries;

Temperature controlled environment means surrounding a first of said sensing capillaries with the second of the sensing capillaries located in said designated environment; and A fluid flow medium within said flow conduit of calibrated temperature and viscosity correlation.

2. An apparatus as described by claim 1 wherein said capillaries represent the dominant flow pressure losses in said conduit.

3. An apparatus as described by claim 1 comprising data processing means for receiving and processing data respective to said calibrated fluid medium correlation and said pressure differentials.

4. An apparatus as described by claim 1 wherein said temperature controlled environment means is a fluid bath means for immersing said first sensing capillary.

5. A method for measuring the temperature of a designated environment comprising the steps of:

Flowing a fluid medium of calibrated temperature and viscosity correlation through a conduit under a constant pressure differential drive;

Restricting the flow of said fluid medium through at least two capillary sections in said conduit;

Measuring the pressure differential across each of said capillary sections;

Surrounding a first of said capillary sections with a thermally controlled environment of known temperature value;

Subjecting a second of said capillary sections to an environment of unknown temperature value; and Determining the value of said unknown temperature from data comprising said measured pressure differentials.

6. A method as described by claim 5 comprising the further steps of:

Converting said capillary section pressure differential measurements to respective electrical signals representing pressure differential data;

Combining the pressure differential data respective to said first capillary section with additional data respective to said calibrated fluid medium to determine the momentary fluid flow rate through said first capillary section.

7. A method as described by claim 6 comprising the further steps of:

Combining the pressure differential data respective to said second capillary section with additional data respective to said momentary fluid flow rate through said first capillary section to determine said unknown temperature value.

8. A method for measuring the temperature of a designated environment comprising the steps of:

Calibrating the temperature and viscosity correlation properties of a fluid medium;

Introducing flow of said fluid medium under a substantially constant pressure drive through a conduit having at least two flow restrictions with substantially high rates of heat exchange;

Controlling the temperature of said fluid medium to a known value at a first of said flow restrictions;

Measuring the pressure differential of said medium flow across said first flow restriction;

Determining the instantaneous flow rate of said fluid medium through said conduit from said first flow restriction pressure differential;

Exposing a second fluid flow restriction to an environment of unknown temperature value;

Measuring the pressure differential of said medium flow across said second flow restriction;

Determining the value of said unknown temperature from said calibrated medium correlation properties, said instantaneous flow rate and said second flow restriction pressure differential.

* * * * *